United States Patent
Dwarakanath et al.

(10) Patent No.: US 9,422,469 B2
(45) Date of Patent: Aug. 23, 2016

(54) MIXED CARBON LENGTH SYNTHESIS OF PRIMARY GUERBET ALCOHOLS

(71) Applicants: Varadarjan Dwarakanath, Houston, TX (US); Robert Shong, Houston, TX (US)

(72) Inventors: Varadarjan Dwarakanath, Houston, TX (US); Robert Shong, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 461 days.

(21) Appl. No.: 13/833,045

(22) Filed: Mar. 15, 2013

(65) Prior Publication Data

US 2014/0262282 A1 Sep. 18, 2014

(51) Int. Cl.
   *C09K 8/584* (2006.01)
   *E21B 43/16* (2006.01)
   *C07C 29/34* (2006.01)
   *C07C 41/03* (2006.01)

(52) U.S. Cl.
   CPC .............. *C09K 8/584* (2013.01); *C07C 29/34* (2013.01); *C07C 41/03* (2013.01); *E21B 43/16* (2013.01)

(58) Field of Classification Search
   CPC ............................... C09K 8/584; E21B 43/16
   See application file for complete search history.

(56) References Cited

U.S. PATENT DOCUMENTS

| | | | |
|---|---|---|---|
| 2,757,139 | A | 7/1956 | Bartlett |
| 4,518,810 | A | 5/1985 | Matsuda et al. |
| 5,298,038 | A | 3/1994 | Hashimoto et al. |
| 5,387,374 | A | 2/1995 | Westfechtel et al. |
| 5,717,119 | A | 2/1998 | O'Lenick, Jr. |
| 6,060,443 | A | 5/2000 | Cripe et al. |

(Continued)

FOREIGN PATENT DOCUMENTS

| | | | | |
|---|---|---|---|---|
| CH | WO 2013167438 A1 | * | 11/2013 | ............. C07C 41/03 |
| DE | WO 2011130310 A1 | * | 10/2011 | ............. C09K 8/584 |

(Continued)

OTHER PUBLICATIONS

Anthony J. O'Lenick, Jr, "A Review of Guerbet Chemistry".
(Continued)

*Primary Examiner* — Angela M DiTrani
*Assistant Examiner* — Crystal J Miller
(74) *Attorney, Agent, or Firm* — Karen R. DiDomenicis; Tiffany Weksberg

(57) ABSTRACT

In an embodiment of the disclosure, mixtures of different carbon length alcohols are used as the primary feedstock for Guerbet alcohols. Specifically, embodiments relate to a method of synthesizing mixed molecular weight surfactants from a mixture of primary alcohols comprising, receiving a mixture of primary alcohols comprising at least two different chain length primary alcohols and reacting the mixture of primary alcohols to produce a mixture of Guerbet alcohols. The mixture of Guerbet alcohols is then used to produce a surfactant composition comprising surfactants of different molecular weights.

9 Claims, 1 Drawing Sheet

(56) References Cited

U.S. PATENT DOCUMENTS

| | | | |
|---|---|---|---|
| 6,234,183 B1* | 5/2001 | Chan | C09K 8/524 134/22.1 |
| 6,342,473 B1* | 1/2002 | Kott | C11D 1/22 510/357 |
| 6,664,429 B1 | 12/2003 | Huebner et al. | |
| 7,119,125 B1* | 10/2006 | O'Lenick, Jr. | B01F 17/0057 516/25 |
| 7,985,718 B2* | 7/2011 | Steinbrenner | C09K 8/584 166/268 |
| 7,989,399 B2* | 8/2011 | Stoian | C09K 8/03 175/64 |
| 8,053,396 B2* | 11/2011 | Huff | B01F 17/0028 166/275 |
| 8,211,837 B2 | 7/2012 | Weerasooriya et al. | |
| 8,524,643 B2* | 9/2013 | Huff | B01F 17/0028 166/270.1 |
| 8,841,241 B2* | 9/2014 | Weerasooriya | C09K 8/584 166/902 |
| 8,946,490 B2* | 2/2015 | Mirk | C07C 29/149 568/885 |
| 2009/0279281 A1 | 11/2009 | Chung et al. | |
| 2011/0071057 A1* | 3/2011 | Weerasooriya | C07D 301/00 507/219 |
| 2011/0220366 A1* | 9/2011 | Bittner | B01F 17/0021 166/369 |
| 2011/0259583 A1* | 10/2011 | Bittner | C09K 8/584 166/270.1 |
| 2011/0263467 A1* | 10/2011 | Bittner | C09K 8/584 507/254 |
| 2013/0068457 A1* | 3/2013 | Thach | C07C 303/24 166/270.1 |
| 2013/0098612 A1* | 4/2013 | Bittner | C09K 8/584 166/279 |
| 2013/0102505 A1* | 4/2013 | Bittner | C09K 8/584 507/254 |
| 2014/0182851 A1* | 7/2014 | Weerasooriya | C09K 8/584 166/270.1 |

FOREIGN PATENT DOCUMENTS

| | | | | |
|---|---|---|---|---|
| EP | 0037542 A2 | 10/1981 | | |
| WO | 2010090901 | 8/2010 | | |
| WO | WO 2011037975 A2 * | 3/2011 | | C07C 29/34 |
| WO | WO 2011130310 A1 * | 10/2011 | | C09K 8/584 |
| WO | 2013/060622 | 5/2013 | | |
| WO | 2013/060623 | 5/2013 | | |
| WO | 2013/060670 | 5/2013 | | |
| WO | 2013/120757 | 8/2013 | | |

OTHER PUBLICATIONS

Lachmann, Goetz; "Sasol Olefins & Surfactants ISFOL® $C_{12}$-$C_{32}$ Defined Branched Guerbet Alcohols"; Oct. 2003, pp. 1-11.
International Search Report, issued on Jun. 12, 2014 during the prosecution of International Application No. PCT/US2014/018221.
Written Opinion of the International Searching Authority, issued on Jun. 12, 2014 during the prosecution of International Application No. PCT/US2014/018221.

* cited by examiner

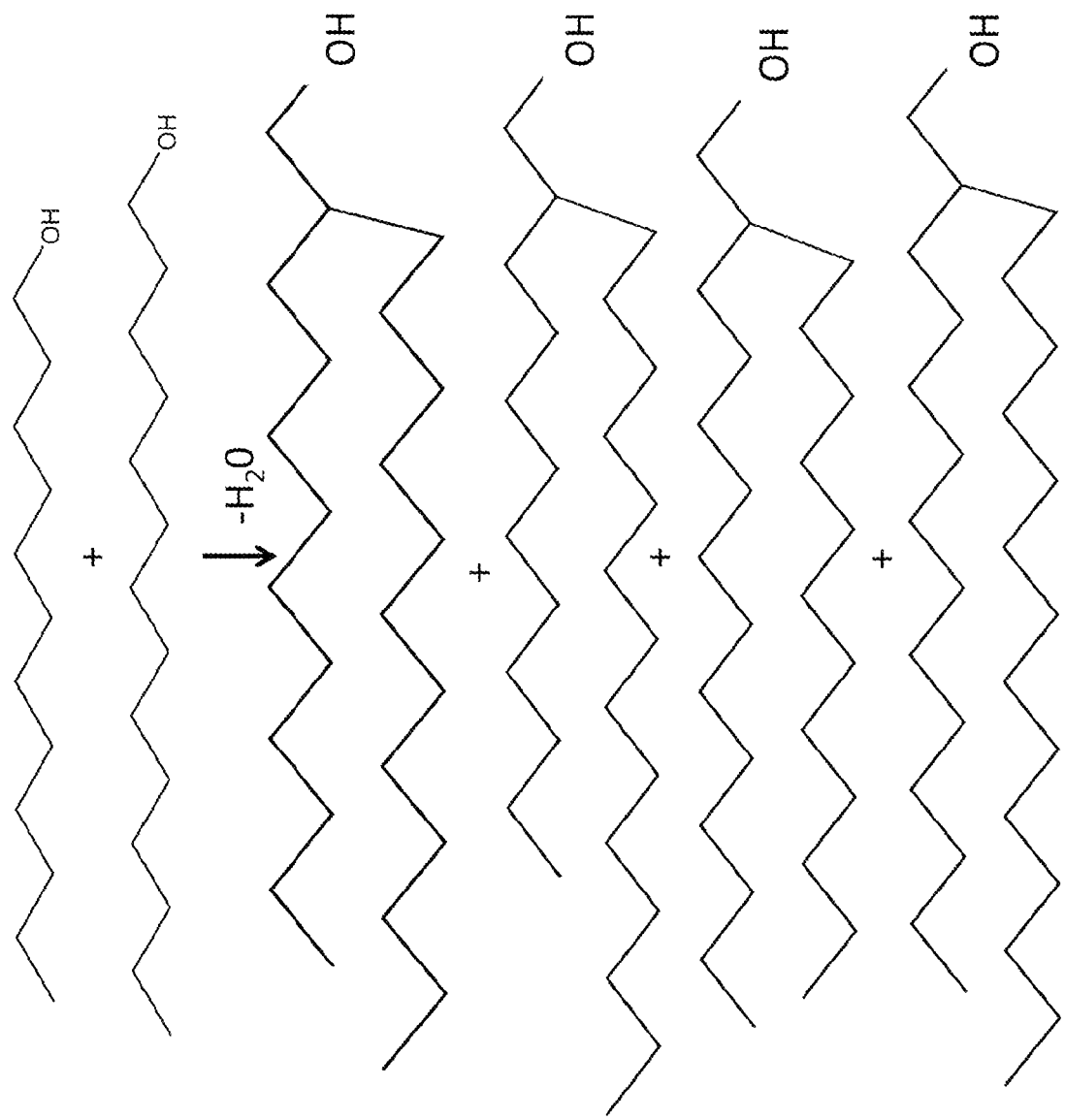

MIXED CARBON LENGTH SYNTHESIS OF PRIMARY GUERBET ALCOHOLS

RELATED APPLICATIONS

The present application is related to the following United States Non-Provisional patent application Ser. No. 13/233,406 entitled "METHOD OF MANUFACTURE OF GUERBET ALCOHOLS FOR MAKING SURFACTANTS USED IN PETROLEUM INDUSTRY OPERATIONS," filed on Sep. 15, 2011, which is assigned or under obligation of assignment to the same entity as this application, and incorporated in this application by reference in full.

TECHNICAL FIELD

The present disclosure generally concerns the field of Guerbet alcohols and the manufacture of surfactants. In particular cases, the present disclosure concerns a method of manufacturing Guerbet alcohols from a mixture of different carbon length hydrocarbons.

BACKGROUND

Guerbet alcohols are high molecular weight primary alcohols with high-purity beta branching. They have low volatility and lower irritation properties compared to other linear alcohols. The melting point and viscosity of Guerbet alcohols are also reduced compared to other linear alcohols. They exhibit oxidative stability at high temperatures and remain liquid up until hydrocarbon chains lengths of $C_{20}$. Furthermore, Guerbet alcohols are reactive and can be used to make many derivatives, such as nonionic surfactants with a wide range of cloud points, which make them particularly suitable for many different petroleum industry operations. However, the products formed from Guerbet alcohols are predominantly used in the cosmetic industry.

The basic starting point of the Guerbet reaction is a fatty alcohol which undergoes self-condensation through the use of strong basis and/or catalysts such as copper or zinc oxide. The produced Guerbet alcohols are beta-branched primary alcohols with twice the molecular weight of the reactant alcohols minus water. The overall reaction for preparing Guerbet alcohols can be represented by the following equation:

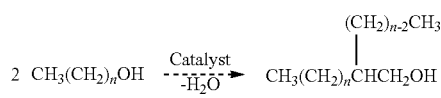

(Equation 1)

wherein subscript indice n is a positive integer greater or equal to 2. For example, if subscript indice n is eleven (11), the reactant alcohol has twelve carbon atoms ($C_{12}$) and the produced Guerbet alcohol has twenty-four carbon atoms ($C_{24}$). Similarly, $C_{16}$ alcohols (n=15) can be combined to make $C_{32}$ Guerbet alcohols. Examples of catalysts that can be used in preparing Guerbet alcohols include nickel, lead salts, oxides of copper, lead, zinc, chromium, molybdenum, tungsten, manganese, palladium compounds, silver compounds, or combinations thereof. Depending on the type of Guerbet alcohol to be produced, dimerization of the reactant alcohol can be carried out at temperatures ranging between about 100 to 300 Degrees Celsius.

For most applications, such as for use in the cosmetics industry, Guerbet alcohols are produced in high purity by driving the reaction (e.g., Equation 1) to near completion. Any unreacted monomer alcohol can be "stripped-off" to further enhance the purity of the produced Guerbet alcohol. As a result, highly branched, high molecular weight primary alcohols with near mid-point branching (i.e., large hydrophobes with high-purity beta branching) are produced. Guerbet alcohols tend to be more expensive than other alcohols due to the comprehensive conversion during the alcohol dimerization process and/or the subsequent removal of unreacted monomer alcohol. Accordingly, the cost of producing Guerbet alcohols can be prohibitive, especially for applications needing large quantities of Guerbet alcohols.

Guerbet alcohols are utilized to manufacture surfactants, which, for example, can be used as wetting agents, emulsifiers, detergents and solubilizers. Surfactants are utilized in various stages of hydrocarbon recovery and processing, such as in drilling operations (e.g., drilling fluids/dispersants), reservoir injection (e.g., fracturing fluids, enhanced oil recovery fluids), well productivity (e.g., acidizing fluids), hydrocarbon transportation, environmental remediation, or a combination thereof. A well-known enhanced oil recovery (EOR) method uses surfactant polymer floods to recover additional oil from reservoirs. The compositions of chemicals used in enhanced oil recovery processes varies depending on the type, environment, and composition of the reservoir formation.

SUMMARY

A general embodiment of the disclosure is a method of synthesizing mixed chain length surfactants from a mixture of primary alcohols comprising, receiving a mixture of primary alcohols comprising at least two different chain length primary alcohols, reacting the mixture of primary alcohols to produce a mixture of Guerbet alcohols, and producing a surfactant composition from the mixture of Guerbet alcohols.

In embodiments, the method of producing the surfactant from the mixture of Guerbet alcohols comprises forming an alkoxylated Guerbet alcohol by reacting a lower weight epoxides with a Guerbet alcohol alkoxylate. In specific embodiments, producing the surfactant composition from the mixture of Guerbet alcohols comprises forming a Guerbet sulfate by sulfation of the Guerbet alcohol alkoxylate, forming a Guerbet sulfonate by sulfonation of the Guerbet alcohol alkoxylate, or forming a Guerbet carboxylate by carboxylation of a Guerbet alcohol alkoxylate.

Embodiments of the surfactant composition may also be used in a petroleum industry operation. For example, the surfactant composition may be used in a petroleum industry operation comprises injecting the surfactant into a subterranean reservoir in an enhanced oil recovery process. In a specific embodiment, the method comprises determining a molecular weight distribution of surfactants for use in a specific reservoir, and determining the ratios of primary alcohols needed to produce Guerbet alcohols with the molecular weight distribution, wherein the received mixture of primary alcohols is of the determined primary alcohol ratio.

The mixture of primary alcohols can comprise two primary alcohols, three primary alcohols, four primary alcohols or five primary alcohols. Further, the mixture of primary alcohols can comprise different primary alcohols in equal ratios or in different ratios. In an embodiment, the reaction of the mixture of primary alcohols to produce a mixture of Guerbet alcohols is stopped when a Guerbet alcohol conversion of at least 80% is obtained, and the unreacted primary alcohols can be removed from the mixture of Guerbet alcohols or can be left in the mixture of Guerbet alcohols.

In additional embodiments of the disclosure, the mixture of primary alcohols is derived from a natural source. In some examples, the natural source is palm oil, algal oil, canola oil, castor bean oil, coconut oil, corn oil, cotton oil, fish oil, flaxseed oil, hempseed oil, jatropha oil, lard, mustard seed oil, nut oil, olive oil, palm kernel oil, peanut oil, rapeseed oil, safflower seed oil, soybean oil, sunflower oil, tall oil, tallow, yellow grease, or any oil produced by using the following: bacteria, yeast, fungi, unicellular organisms, and multicellular organisms.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 is an example of a mixed Guerbet reaction illustrating the structures of the starting materials and the products for the reaction of $CH_3(CH_2)_{10}CH_2OH + CH_3(CH_2)_{12}CH_2OH \rightarrow CH_3(CH_2)_{22}CH_2OH + CH_3(CH_2)_{24}CH_2OH + CH_3(CH_2)_{26}CH_2OH$. The reaction with equal moles of alcohol generates the production ration of 1:2:1 $C_{24}OH:C_{26}OH:C_{28}OH$.

DETAILED DESCRIPTION

Detailed Description of the Invention

Aspects of the present invention describe a method for manufacturing large molecular-weight surfactants from branched Guerbet alcohols (GAs) derived from a mixture of different carbon length alcohols. As will be described, the surfactants and Guerbet alcohols of the present disclosure conform to a specific ratio given the length of the different reacting hydrocarbons and their starting reaction ratios.

As previously described, in the Guerbet reaction, two alcohols are reacted with or without a catalyst to produce an alcohol which has double the molecular weight of the reactant alcohols. Commercially available Guerbet Alcohols use a single primary alcohol to obtain the double molecular weight structure. However, embodiments disclosed here use a mixture of different carbon length alcohols as the starting material to form a product with a mixture of different length Guerbet alcohols. The reaction of different chain length alcohols, such as $C_{10}$ to $C_{18}$, forms Guerbet Alcohol products of molecular weight distributions based on the possible carbon ratio combinations. For example a 1:1 mixture of a $C_{12}$ and $C_{14}$ primary alcohol will produce a 1:2:1 mixture of $C_{24}$, $C_{26}$, and $C_{28}$ Guerbet alcohols, respectively (see FIG. 1). The mixed chain length Guerbet Alcohols can be further modified by oxylating the primary alcohol group with ethylene and propylene oxide, etc. These can also be sulfated, sulfonated, carboxylated, etc. in order to produce a surfactant composition that comprises surfactants with different carbon lengths. Unreacted species may be left in the mixture, further reducing the cost of manufacture.

As used herein, "a" or "an" means "at least one" or "one or more" unless otherwise indicated.

As used herein, the term "essentially equal" or "about," refers to equal values or values within the standard of error of the device that is used to measure the value. The term "substantially equal," as used herein, refers to an amount that is within 3% of the value recited.

As used herein a "Guerbet alcohol" refers to a primary alcohol with beta branching that has been produced using a Guerbet synthesis reaction.

As used herein a "Guerbet surfactant" refers to a surfactant produced from a Guerbet alcohol.

In an embodiment of the disclosure, mixtures of different carbon length alcohols are used as the primary feedstock for Guerbet alcohols. These feedstock mixtures result in a distribution of different carbon lengths which, when sulfonated, carboxylted, etc., presents superior enhanced oil recovery properties to the mixture of surfactant.

Conventional Guerbet reactions use a pure primary alcohol chain, from $C_{10}$ to $C_{18}$, which is then reacted with itself. However, embodiments of the invention use a mixture of primary alcohols from $C_{10}$ to $C_{30}$ which is reacted to form a mixture of different carbon chain length Guerbet alcohols. For example, the mixture may comprise $C_{10}$ and $C_{12}$ or the mixture could also comprise $C_{14}$ and $C_{18}$. The two or more primary alcohols are converted to a mixed Guerbet Alcohol by reacting with a metal catalyst and base, for example. The alcohols, catalyst, and base mixture is stirred and heated to Guerbet reaction temperatures (220-300° C.) with nitrogen purging to remove produced water. The reaction is continued until a Guerbet alcohol conversion of at least about 50%, at least about 60%, at least about 70%, at least about 80%, at least about 85%, at least about 90%, at least about 95%, or about 100% is obtained by measuring the loss of reactant alcohols. The reaction mixture may then be filtered to remove the metal catalyst and/or the unreacted base.

The mixture of different length primary alcohols used as feedstock for the Guerbet alcohols may come from a variety of sources. For example, the primary alcohols may be derived from mineral hydrocarbon sources or they may be derived from biologically based sources, providing for a "green" starting material. The "green" starting material could be used without need for excessive cleaning or separation, reducing the environmental foot print and the price of processing the material. The biologically based source may be a bio-lipid, such as a triglyceride. The biologically based sources include palm oil, algal oil, canola oil, castor bean oil, coconut oil, corn oil, cotton oil, fish oil, flaxseed oil, hempseed oil, jatropha oil, lard, mustard seed oil, nut oil, olive oil, palm kernel oil, peanut oil, rapeseed oil, safflower seed oil, soybean oil, sunflower oil, tall oil, tallow, yellow grease, or any oil produced by using the following: bacteria, yeast, fungi, unicellular organisms, and multicellular organisms.

There are many processes for breaking down triglyceride bonds to convert the aforementioned bio-lipids to fatty acid alkyl esters such as transesterification, blending, microemulsions, and pyrolysis. Transesterification is the most common method used for producing fatty acid alkyl esters from bio-lipid. The term "transesterification" (as well as derivatives, other forms of this term, and linguistically related words and phrases), as used herein, generally refers to the process of forming an ester by reacting one or more fatty acids with an alcohol, typically in the presence of a catalyst. More specifically, this term refers to the process of converting bio-lipids to fatty acid alkyl esters and glycerin. Generally, the bio-lipid raw materials, or the fatty acids and triglycerides obtained after subjecting the bio-lipid raw materials to separation, are reacted with a low-molecular weight alcohol in the presence of a catalyst to produce fatty acid alkyl esters and glycerin. In most applications, the low-molecular weight alcohol is methanol or ethanol. Other possible low-molecular weight alcohols include propanol and butanol. Catalysts accelerate the chemical reaction by reducing the activation energy (i.e., the energy needed to initiate the reaction). Examples of catalysts (or biocatalysts) include acids (e.g., hydrochloric acid, sulfuric acid, sulfonic acid, heteropoly acid, a Lewis acid, a Brønsted acid), a Brønsted acidic ionic liquid, organic or inorganic bases, enzymes, lipase, and an alkoxide, a carbonate, or a hydroxide of sodium, potassium, calcium, or barium. Sodium hydroxide (NaOH), potassium hydroxide (KOH), sodium methoxide ($NaOCH_3$), and potassium methoxide ($KOCH_3$) are the most common alkali catalysts used for transesterification.

The fatty acid alkyl esters, such as fatty acid methyl ester, are then reduced to fatty alcohols (natural alcohols), which typically are aliphatic alcohols having a chain of 8 to 22 carbon atoms. In one embodiment, the esters of fatty acids are hydrogenated using a catalyst, such as copper chromite.

In some embodiments of the disclosure, the alcohol feedstock mixture consists of two different length primary alcohols, three different length primary alcohols, four different length primary alcohols, five different length primary alcohols, six different length primary alcohols, or seven or more different length primary alcohols. The primary alcohols can be $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or more than 30 carbon atoms long. The chain lengths may be even, odd, or a combination thereof. The alcohols to be reacted with each other may also include chains of ethylene oxide or propylene oxide. The mixture of primary alcohols may be made from mixing different length primary alcohols together, or the mixture of primary alcohols may occur naturally. For example, primary alcohols derived from the fatty acids from palm oil naturally comprise a mixture of $C_{16}$ and $C_{18}$.

In one embodiment of the disclosure, the mixed Guerbet alcohols are utilized to manufacture surfactants, which, for example, can be used as wetting agents, emulsifiers, detergents and solubilizers. In some embodiments, Guerbet alcohols are sulfated to obtain Guerbet sulfates. For example, sulfamic acid sulfation can be used. In some embodiments, Guerbet alcohols are sulfonated to obtain Guerbet sulfonates. Alkoxylated Guerbet alcohols can also undergo sulfation or sulfonation to produce large, branched C24-C32 alkyl alkoxylated surfactants, such as alkyl sulfate surfactants or alkyl sulfonates surfactants. These surfactants can also be tailored to exhibit desirable phase behaviors for particular reservoir conditions by altering the molecular weight, molecular weight distribution, and branching/point of attachment (e.g., attachment of aryl groups to alkyl groups). The mixed Guerbet alcohols may also be carboxylated to yield a carboxylate surfactant.

One example of a surfactant that can be manufactured from a Guerbet alcohol is an anionic surfactant. Some anionic surfactants, such as sulfates, sulfonates, phosphates, and carboxylates are described in the art in, for example, SPE 129907 and U.S. Pat. No. 7,770,641, which are both incorporated herein by reference. Non-ionic surfactants include alcohol alkoxylates such as alkylaryl alkoxy alcohols or alkyl alkoxy alcohols. In some embodiments, non-ionic surfactants manufactured form Guerbet alcohols are combined with other non-ionic surfactants such as non-ionic esters.

In some embodiments the Guerbet alcohols are alkoxylated to form alkoxylated Guerbet alcohols. Here, lower weight epoxides, such as ethylene oxide (EO), propylene oxide (PO), and butylenes oxide (BO), are added to the Guerbet alcohols. In some embodiments, more than six (6) repeating units, such as EO, are present. In some embodiments, more than ten to twenty repeating units, such as EO, are present. In embodiments, there are less than 35 EO and less than 10 PO, or a mixture thereof. These lower weight epoxides are typically used to tailor the surfactant such that it exhibits a desirable phase behavior for particular reservoir conditions, such as electrolyte concentrations (salinities), temperature, and hydrocarbon compositions. Accordingly, a desired HLB (Hydrophillic-Lipophillic-Balance) can be achieved by tailoring the number of alkoxylates attached to the Guerbet alcohol, as well as tailoring the ratios of the feedstock primary alcohols in the mixture.

In embodiments of the disclosure, the mixed length Guerbet surfactants disclosed herein provide enhanced phase behavior and solubility profiles for use in surfactant polymer floods during enhanced oil recovery methods. Once a mixed length surfactant composition has been optimized for a specific formation, the ratios of the starting alcohols can be back calculated to produce the specific ratios of surfactant lengths needed. In this way, mixed length surfactant compositions can be tailor made for specific reservoir conditions.

In an embodiment of the disclosure, the use of mixed length alcohols as the starting point for Guerbet alcohols results in a faster reaction rate than found using a pure alcohol as the starting point. Pure Guerbet reactions have been found to yield 60% product in 24 hours, while Guerbet reactions with mixed length starting alcohols can result in 90% yield in 23 hours (See Example 1).

In one embodiment, surfactants are utilized for environmental treatment of wastes (ex situ and/or in situ). In particular, at least one surfactant manufactured using mixed Guerbet alcohols is used to enhance chemical treatment of contaminated soil or sediment. The contaminant may be organic, such as oil or solvent, or inorganic, such as mercury and arsenic. The surfactant reduces the interfacial tension between oil and water, thereby increasing the solubility of the contaminant.

EXAMPLES

The following examples are included to demonstrate specific embodiments of the disclosure. It should be appreciated by those of skill in the art that the techniques disclosed in the examples that follow represent techniques discovered by the inventors to function well in the practice of the invention, and thus, can be considered to constitute modes for its practice. However, those of skill in the art should, in light of the present disclosure, appreciate that many changes can be made in the specific embodiments disclosed and still obtain a like or similar result without departing from the spirit and scope of the invention.

Example 1

Guerbet Reaction of Mixed Primary Alcohols

This Example covers seven different reactions, each using a different starting mixture of primary alcohols. Table 1 contains the overview of reactants, products and reaction parameters used for the seven different reactions numbered 1-7. Each reaction used 500 grams of the starting reactant mixture at the specified reactant ratio, which was loaded into a reactor with about 0.5 grams of Cu/Ni 80/20 metal powder and 8-9 grams potassium hydroxide (KOH). The reactor was then purged with $N_2$ and heated to the amount specified in the table. The reaction proceeded at 1 atm. Samples were pulled every hour to determine the yield. The yield was calculated by measuring the loss of reactants (starting material) with GC gas chromatography. The starting materials in reactions 6 and 7 were prepared from biologically derived alcohols. The starting material in reaction 6 was derived from a bacterially produced fatty acid, while the starting material for reaction 7 was derived from palm oil.

TABLE 1

| No. | Starting Mixture | Reactant Ratio | Products Found | Product Ratio | % Yield | Rxn Time (Hrs.) | Temp. ° C. |
|---|---|---|---|---|---|---|---|
| 1 | C12H26O, C14H28O | 1:1 | C24, C26, C28 | 1:2:1 | 85 | 32 | 236 |
| 2 | C12H26O, C14H28O | 1:1 | C24, C26, C28 | 1:2:1 | 90 | 59 | 240 |
| 3 | C10H22O, C12H26O, C14H28O | 1:1:1 | C20, C22, C24, C26, C28 | 1:2:4:3:1 | 90 | 23 | 239 |
| 4 | C10H22O, C12H26O, C14H28O, C16H34O | 1:1:1:1 | C20, C22, C24, C26, C28, C30, C32 | 1:3:5:7:5:2:1 | 84 | 31 | 250 |
| 5 | C10H22O, C12H26O, C14H28O | 1:1:1 | C20, C22, C24, C26, C28 | 1:4:4:3:1 | 58 | 18 | 228 |
| 6 | C12H26O, C14H28O | 3.8:1 | C24, C26, C28 | 16:8:1 | 88 | 27 | 242 |
| 7 | C12H26O, C14H28O | 3:1 | C24, C26, C28 | 8:5:1 | 80 | 40 | 237 |

Although the present invention and its advantages have been described in detail, it should be understood that various changes, substitutions and alterations can be made herein without departing from the spirit and scope of the invention as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications mentioned in the specification are indicative of the levels of skill in the art to which the invention pertains. All patents and publication are herein incorporated by reference to the same extent as if each individual publication was specifically and individually indicated to be incorporated by reference.

"A Review of Guerbet Chemistry" by Anthony J. O'Lenick, jr;
U.S. Pat. No. 2,757,139
U.S. Pat. No. 4,518,810
U.S. Pat. No. 5,298,038
U.S. Pat. No. 5,717,119
U.S. Pat. No. 5,387,374
U.S. Pat. No. 6,060,443
U.S. Pat. No. 8,211,837

What is claimed is:

1. A method of synthesizing mixed chain length surfactants from a mixture of primary alcohols, the method comprising:
   receiving a mixture of primary alcohols comprising greater than two different chain length primary alcohols in equal parts of each primary alcohol;
   reacting in a single reactor the mixture of primary alcohols to produce a mixture of at least five Guerbet alcohols having different molecular weights wherein:
   i. the number of Guerbet alcohols produced is equal to twice the number of primary alcohols minus one;
   ii. the mixture of at least five Guerbet alcohols comprises a lowest molecular weight Guerbet alcohol, a highest molecular weight Guerbet alcohol, a Guerbet alcohol having a molecular weight halfway between the molecular weight of the lowest molecular weight Guerbet alcohol and the highest molecular weight Guerbet alcohol;
   iii. the Guerbet alcohol having the molecular weight halfway between the molecular weight of the lowest molecular weight Guerbet alcohol and the highest molecular weight Guerbet alcohol has a highest concentration of the Guerbet alcohols in the mixture of at least five Guerbet alcohols;
   iv. the lowest molecular weight Guerbet alcohol and the highest molecular weight Guerbet alcohol each have a lowest concentration of the Guerbet alcohols in the mixture of at least five Guerbet alcohols; and
   v. remaining Guerbet alcohols in the mixture of at least five Guerbet alcohols have concentrations increasing as molecular weight approaches the molecular weight halfway between the molecular weight of the lowest molecular weight Guerbet alcohol and the highest molecular weight Guerbet alcohol and decreasing as molecular weight approaches the lowest and the highest molecular weight Guerbet alcohols; and producing a surfactant composition from the mixture of greater than two Guerbet alcohols;

wherein the mixture of primary alcohols is derived from a natural source selected from the group consisting of palm oil, algal oil, canola oil, castor bean oil, coconut oil, corn oil, cotton oil, fish oil, flaxseed oil, hempseed oil, jatropha oil, lard, mustard seed oil, nut oil, olive oil, palm kernel oil, peanut oil, rapeseed oil, safflower seed oil, soybean oil, sunflower oil, tall oil, tallow, yellow grease, and any oil produced by using the following: bacteria, yeast, fungi, unicellular organisms, multicellular organisms or a combination thereof;

wherein the reacting the mixture of primary alcohols to produce the mixture of greater than two Guerbet alcohols is stopped when a Guerbet alcohol conversion of at least 80% is obtained; and wherein unreacted primary alcohols are removed from the mixture of greater than two Guerbet alcohols.

2. The method of claim 1, wherein the producing the surfactant from the mixture of greater than two Guerbet alcohols comprises forming an alkoxylated Guerbet alcohol by reacting a lower weight epoxide with a Guerbet alcohol alkoxylate.

3. The method of claim 1, wherein the producing the surfactant surfactant composition from the mixture of greater than two Guerbet alcohols comprises comprises forming a Guerbet sulfate by sulfation of a Guerbet alcohol alkoxylate.

4. The method of claim 1, wherein the producing the surfactant composition from the mixture of greater than two Guerbet alcohol comprises forming a Guerbet sulfonate by sulfonation of a Guerbet alcohol alkoxylate.

5. The method of claim 1, further comprising injecting the surfactant composition into a subterranean reservoir in an enhanced oil recovery process.

6. The method of claim 1, wherein the mixture of primary alcohols comprises three primary alcohols, four primary alcohols, five primary alcohols, six primary alcohols or seven primary alcohols.

7. The method of claim 1, wherein the mixture of primary alcohols comprises greater than two different primary alcohols in equal ratios.

8. The method of claim 1, wherein the mixture of primary alcohols comprises greater than two different primary alcohols in different ratios.

9. The method of claim 1, wherein the producing the surfactant composition from the mixture of greater than two Guerbet alcohols comprises forming a Guerbet carboxylate by carboxylation of a Guerbet alcohol.

* * * * *